United States Patent [19]

Sanchez

[11] Patent Number: 5,516,856

[45] Date of Patent: May 14, 1996

[54] PROCESS FOR THE USE OF ANTIOXIDANT-PEROXIDES TO CURE AND ENHANCE THE STABILITY OF POLYMERS

[75] Inventor: Jose Sanchez, Grand Island, N.Y.

[73] Assignee: Elf Atochem North America, Inc., Philadelphia, Pa.

[21] Appl. No.: 375,213

[22] Filed: Jan. 18, 1995

Related U.S. Application Data

[63] Continuation of Ser. No. 96,197, Jul. 22, 1993, abandoned, which is a continuation of Ser. No. 750,385, Aug. 27, 1991, abandoned, which is a division of Ser. No. 200,340, May 31, 1988, Pat. No. 5,051,531.

[51] Int. Cl.$^6$ .............................. C08F 20/10; C08F 4/34; C08F 4/36; C08L 27/22; C08L 43/00; C08L 33/06; C08L 9/00; C08L 33/18; C08L 23/26

[52] U.S. Cl. .................. 525/447; 525/224; 525/232; 525/238; 525/240; 525/199; 525/209; 525/213; 526/232

[58] Field of Search .................... 525/447, 199, 525/209, 213, 224, 232, 238, 240; 526/232

[56] References Cited

U.S. PATENT DOCUMENTS

| | | |
|---|---|---|
| 3,236,872 | 2/1966 | Manly et al. |
| 3,488,392 | 1/1970 | McKellin |
| 3,862,064 | 1/1975 | Fry ................................ 525/49 |
| 3,988,509 | 10/1976 | Ballard et al. |
| 4,460,750 | 7/1984 | Thiersault et al. |
| 4,525,308 | 6/1985 | Sanchez |
| 4,634,753 | 1/1987 | Sanchez ............................ 526/216 |
| 4,683,248 | 7/1987 | Rauer et al. |
| 4,705,888 | 11/1987 | Meijer et al. ....................... 560/302 |

OTHER PUBLICATIONS

A. M. Hucek, J. T. Barbas, and J. E. Leffler, J. Am. Chem. Soc. 95(14), 4698–4705, 1973.

"Peroxides and Peroxy Compounds, Organic," Kirk–Othmer: Encyclopedia of Chemical Technology, vol. 17, 3rd Ed., pp. 27–90, John Wiley & Sons, Inc., (1982).

T. H. Fisher et al., "Anchimerically Accelerated Bond Homolysis. VI. The Mechanism of Sulfur Participation on Perester Oxygen", *Journal of the American Chemical Society*, 88:3382–3388 (1966).

Paul P. Nicholas et al., "Antioxidants and Antiozonants", *Kirk–Othmer Encyclopedia of Chemical Technology*, 3rd Ed., vol. 3, pp. 128–148 (1978).

J. A. Kuczkowski et al., "Polymer–Bound Antioxidants", *Rubber Chemistry and Technology*, vol. 57, pp. 621–651 (1984).

L. D. Freedman et al., "Antioxidants and Antiozonants", *Kirk–Othmer Encyclopedia of Chemical Technology*, 3rd Ed., vol. 3, pp. 128–148 (1978).

A. M. Hucek, J. T. Barbas, and J. E. Leffler, J. Am. Chem. Soc. 95(14), 4698–4705, 1973.

Organic Peroxides, vol. 1, Daniel Swern, Ed., Chapter V. (Peroxyesters) by Lawrence A. Singer, pp. 265–312, Wiley Interscience, New York, 1970.

*Primary Examiner*—Joseph L. Schofer
*Assistant Examiner*—Wu C. Cheng

[57] ABSTRACT

The present invention relates to a novel antioxidant-peroxide compound of Structure A, $$(Y-[-R-OO-X]_x-An]_y \qquad A$$

in which the definitions of X, Y, R, An, x, and y are given in the Summary of the Invention section, for example, t-butyl peroxy-3-(3,5-di-t-butyl-4-hydroxyphenyl)propionate, processes for producing polymeric compositions of enhanced oxidative stability via initiation of polymerization of ethylenically unsaturated monomers, curing of elastomers and unsaturated polyester resins, modification of polypropylene and other polymers and copolymers, and crosslinking of olefin polymers and copolymers, and the resulting polymers having enhanced oxidative stability.

32 Claims, No Drawings

PROCESS FOR THE USE OF ANTIOXIDANT-PEROXIDES TO CURE AND ENHANCE THE STABILITY OF POLYMERS

CROSS-REFERENCE TO RELATED APPLICATIONS

This application is a continuation of application Ser. No. 08/096,197, filed Jul. 22, 1993, now abandoned, which was a continuation of application Ser. No. 07/750,385, filed Aug. 27, 1991, now abandoned, which in turn was a divisional of U.S. application Ser. No. 07/200,340, filed May 31, 1988, now U.S. Pat. No. 5,051,531.

BACKGROUND OF THE INVENTION

1. Field of the Invention

This invention relates to novel antioxidant-peroxides (AO-P's) and the use of AO-P's for producing polymeric compositions of enhanced oxidative stability via initiation of polymerization of ethylenically unsaturated monomers, curing of elastomers and unsaturated polyester resins, modification of polypropylene and propylene copolymers, and crosslinking of ethylene polymers and copolymers.

2. Description of the Prior Art

Many polymers undergo oxidative degradation to varying degrees during processing fabrication and/or during the intended lifetime of the articles fabricated from them. Typically, antioxidant compounds are added to polymeric materials in order to protect them during processing as well as during their use. Generally, such antioxidant compositions consist of one or more compounds selected from hindered phenols, sulfides, amino, hydrazido, and phosphorous III (phosphites, phosphonites, etc.) compounds. In many cases combinations of hindered phenols and sulfides exhibit synergy when used with certain polymeric systems, (Kirk-Othmer Encyclopedia of Chemical Technology, "Antioxidants and Antiozonants," Third Edition, Vol. 3, pp. 128–148 (1978)). The same reference describes various types of antioxidants that are employed for suppressing the oxidation of foods, petroleum products and polymers (natural, as well as synthetic). This reference also describes the mechanisms of antioxidant actions.

However, not all antioxidants operate by the same antioxidant mechanism. Hindered phenol antioxidants such as 2,6-di-t-butyl-4-methylphenol and secondary arylamines react rapidly with reactive free radicals on the backbone of the polymer and thus prevent the formation of labile hydroperoxide groups along the backbone of the polymer chain. Dialkyl sulfides (e.g., dialkyl thiodipropionates), trialkyl and triaryl phosphites and metal salts of sulfur compounds (e.g., zinc dithiocarbamates, zinc dithiophosphates and zinc xanthates) suppress oxidation of polymers by reacting with hydroperoxy groups, thus producing non-peroxidic species.

Many of the antioxidants developed commercially are fugitive in nature, that is, they are extractible from the compositions with which they are used, owing to their relatively low molecular weights and the relatively high temperatures required for processing the polymers in which they are employed. In addition, many potential antioxidants are easily extracted by solvents from the host polymer.

There has been considerable effort in recent years to develop non-fugitive antioxidants. Such antioxidants are referred to as non-fugitive antioxidants, since they do not leach out or are not extractible from the polymer or other composition to which they are added, either during processing or during the end use of the composition.

One of the reasons for this emphasis is the need to fabricate polymeric articles that must pass stringent United States Food and Drug Administration extraction tests in order to qualify the polymeric composition for use in food and drug applications. Another reason for non-fugitive antioxidants is the trend to higher processing temperatures which results in larger losses of conventional lower molecular weight antioxidants. Losses during polymer processing results in greater costs for the antioxidant and exposes workers, the public and the environment to possibly toxic materials.

The main approaches to achieving non-fugitive antioxidants were to significantly increase the molecular weight of the antioxidant by attaching several antioxidant moieties to one compound or by attaching antioxidant moieties to high molecular weight compounds (e.g., polymers).

One approach to making antioxidants non-fugitive is to covalently bond the antioxidant to the polymer. J. A. Kuczkowski and J. G. Gillick, "Polymer-Bound Antioxidants", *Rubber Chemistry and Technology*, Vol. 57, pages 621–651 (1984), disclose approaches for attaching of antioxidants to polymers. The approaches include preparation, polymerization and copolymerization of antioxidants possessing free radically polymerizable, ethylenically unsaturated groups and reaction between antioxidants and polymers possessing co-reactive groups.

The Kirk-Othmer Encyclopedia of Chemical Technology Third Edition, Vol. 17, "Peroxides and Peroxy Compounds, Organic", pp. 27–90 (1982), also describes various types of organic peroxides and peroxy compounds and their uses for producing and modifying polymeric materials.

T. H. Fisher and J. C. Martin, J. Am. Chem. Soc. 88, p. 3382 (1966), reports the decomposition kinetics for t-butyl peroxy-2-(phenylthio)benzoate and t-butyl peroxy-2,6-di-(phenylthio)benzoate. Owing to the proximity of the sulfur group to the peroxide group, accelerated rates of decompositions were observed for these peroxyesters compared to the analogs without sulfur groups. The use of these sulfur-containing peroxyesters as AO-P's was not suggested by the authors.

Diperoxyketals possessing sulfide (—S—), sulfoxide (—SO—) and sulfone (—$SO_2$—) moieties are disclosed in U.S. Pat. No. 3,488,392. The structure of the novel AO-P's of this invention does not cover these sulfur containing peroxyesters or diperoxyketals.

The chemical literature does not disclose the preparations of antioxidant-peroxides (AO-P's) of the hindered phenol type and the use of these novel compounds for producing polymeric compositions of enhanced oxidative stability via initiation of polymerization of ethylenically unsaturated monomers, curing of elastomers and unsaturated polyester resins, modification of polypropylene and propylene copolymers, and crosslinking of ethylene polymers and copolymers. It is surprising that the novel AO-P's of the present invention are useful, dual functional compounds in view of the fact that the organic peroxide and the antioxidant are at cross purposes with each other (generation of free radicals and deactivation of free radicals, respectively). One skilled in the art would be discouraged to prepare and find useful compounds and compositions with antioxidant and peroxide functions in the same molecule. In these processes the antioxidant becomes covalently bound to the polymer thereby making the antioxidant non-fugitive.

SUMMARY OF THE INVENTION

The present invention is based upon the surprising discovery that, whereas antioxidants enhance oxidative stability of elastomers and thermoplastics by trapping undesirable free radicals before they can cause chain degradation, etc., the novel antioxidant-peroxides (AO-P's) of this invention are effective in initiating the free radical polymerization of ethylenically unsaturated monomers, the free radical curing of unsaturated polyester resin compositions and elastomers, the free radical crosslinking of ethylene homopolymers and copolymers and the free radical modification of polypropylene and propylene copolymers. These results are surprising in view of the fact that the AO-P's and their decomposition products possess antioxidant (AO) moieties that trap free radicals. Furthermore, the AO-P's of this invention produce resins having enhanced oxidative stabilities.

For instance, the compound t-butyl peroxy-3-(3,5-di-t-butyl-4-hydroxyphenyl)-propionate, otherwise known by its International Union of Pure and Applied Chemistry (IUPAC) name, t-butyl 3-(3,5-di-t-butyl-4-hydroxyphenyl)peroxypropionate, an AO-P of this invention including a peroxyester group and a hindered phenol group, when used as a curing agent for polybutadiene (PBD), cured the PBD resin and imparted enhanced oxidative stability to the cured PBD. Furthermore, this compound also effectively cured an unsaturated polyester resin. These results surprisingly demonstrate that in spite of the presence of the hindered phenol group in this compound, free radicals are produced which result in curing of PBD and the unsaturated polyester resin.

One aspect of the present invention is a novel antioxidant-peroxide of structure A:

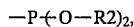

(Y—[—R—OO—X)$_x$—An]$_y$      A where x and y are 1 or 2, but when x is 2, y can only be 1, and when y is 2, x can only be and with the following provisos (I), (II) and (III):

(I) when x is 1 and y is 1,

An is an antioxidant monoradical having a structure (1), (2) or (3):

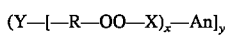

(1)

where
R1 is a t-alkyl radical of 4 to 8 carbons;
R11 is a structure

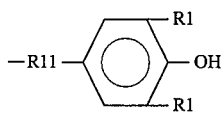

where R12 is an alkylene diradical of 1 to 6 carbons, preferably of 1 to 3 carbons, or an alkenylene diradical of 2 to 6 carbons, preferably of 2 to 4 carbons, and where R13 is an alkylene diradical of 1 to 3 carbons, or a substituted or unsubstituted 1,2-phenylene diradical, the substituents being one or more lower alkyl radicals of 1 to 4 carbons, chloro, bromo, fluoro, carboxy or nitro; or

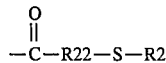

(2)

or

—P(—O—R2)$_2$,      (3)

where
R2 is an alkyl radical of 1 to 18 carbons, an aryl radical of 6 to 12 carbons, and
R22 is an alkylene diradical of 1 to 6 carbons or an alkenylene diradical of 2 to 6 carbons;
Y is nothing;
R is a t-alkyl radical of 4 to 10 carbons, a t-aralkyl radical of 9 to 13 carbons, an acyl radical of 2 to 13 carbons, an aroyl radical of 7 to 11 carbons, an alkoxycarbonyl radical of 2 to 13 carbons, or the radical

An—X—;

and,
X is a direct bond or the diradicals

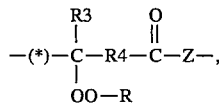

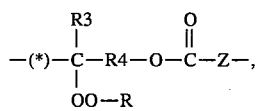

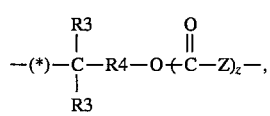

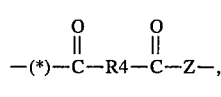

or

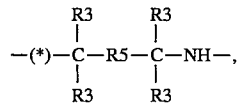

where the —(*)— shows the point of attachment of the —OO— grouping to the —X— diradical, the other end of the —X— diradical being attached to the An radical,
where
R3 is a lower alkyl radical of 1 to 4 carbons,
R4 is an unsubstituted or lower alkyl substituted alkylene diradical of 2 to 4 carbons,
R5 is a substituted or unsubstituted 1,3- or 1,4-phenylene diradical, substituents being lower alkyl, chloro or bromo,
—Z— is the diradical

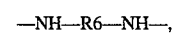

—NH—R6—NH—, where
R6 is nothing, a substituted or unsubstituted alkylene diradical of 2 to 10 carbons or a substituted or unsubstituted 1,2-, 1,3- or 1,4-phenylene diradical, substituents being lower alkyl, chloro or bromo, and
z is 0 or 1;

(II) when x is 1 and y is 2,
An is the same as when x is 1 and y is 1;
Y is an alkylene diradical of 2 to 4 carbons or an ethynylene diradical;
X is a direct bond and R is the alkylidene diradical

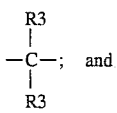

(III) when x is 2 and y is 1,
An is an antioxidant diradical having the structure

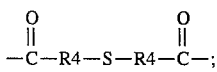

Y is nothing;

R is a t-alkyl radical of 4 to 10 carbons, a t-aralkyl radical of 9 to 13 carbons, an acyl radical of 2 to 13 carbons, an aroyl radical of 7 to 11 carbons, or an alkoxycarbonyl radical of 2 to 13 carbons; and X is the same as when x is 1 and y is 1.

Other aspects of the present invention include:

A. Novel processes using the AO-P's of structure A as free radical initiators for polymerizing ethylenically unsaturated monomers (such as styrene, ethylene and vinyl chloride) by the use of initiating amounts of the AO-P's of structure A under appropriate reaction conditions;

B. Novel processes using the AO-P's of structure A as curing agents for the curing of elastomers (ethylene-propylene copolymers, ethylene-propylene-diene terpolymers, butadiene rubbers, etc.) by reacting such resins with initiating amounts of the AO-P's of structure A under appropriate reaction conditions;

C. Novel processes using the AO-P's of structure A as curing agents for the curing of unsaturated polyester resin compositions by reacting such resins with initiating amounts of the AO-P's of structure A under appropriate reaction conditions;

D. Novel processes using the AO-P's of structure A for modifying (i.e., reducing the molecular weight and broadening the molecular weight distribution of) polypropylene and other polymers by reacting such resins with modifying amounts of the AO-P's of structure A under appropriate reaction conditions;

E. Novel processes using the AO-P's of structure A for crosslinking of olefin polymers (e.g., low density polyethylene, linear low density polyethylene, high density polyethylene, etc.) by reacting such resins with crosslinking amounts of the AO-P's of structure A under appropriate reaction conditions; and F. Polymers having enhanced oxidative stabilities as a result of processes A., B., C., D. and E.

The reaction conditions of the above-summarized processes, such as temperature, pressure, addition rates, reaction times, etc. would be well known to those skilled in the art based on the disclosure herein, or readily discernible without undue experimentation.

DETAILED DESCRIPTION OF THE PREFERRED EMBODIMENTS

Preparation of the Antioxidant-Peroxides (AO-P's)

In general, the AO-P's of structure A of this invention can be prepared by reacting antioxidants (AO's) possessing reactive acid halide and chloroformate groups with a t-alkyl hydroperoxide, or by reacting AO's possessing reactive groups (acid halide, chloroformate, hydroxy, etc.) with peroxy compounds possessing co-reactive groups (hydroxy, amino, hydrazino, acid chloride, chloroformate, etc.), usually in the presence of a basic compound.

In general, the basic compounds are inorganic bases, such as sodium hydroxide, potassium hydroxide, lithium hydroxide, sodium carbonate, potassium carbonate, sodium hydrogen carbonate and potassium hydrogen carbonate, and organic amines, such as pyridine, N,N-dimethylaniline, triethylamine, tributylamine and 1,4-diazabicyclo(2.2.2)octane.

AO's possessing acid halide or chloroformate or other reactive halide groups include for example, without limitation, compounds such as:

3,5-di-t-butyl-4-hydroxybenzoyl chloride,
3-(3,5-di-t-butyl-4-hydroxyphenyl)propionyl chloride,
3,5-di-t-butyl-4-hydroxybenzoyl bromide,
methylmercaptopropionyl chloride,
n-hexylmercaptopropionyl chloride,
n-dodecylmercaptopropionyl chloride,
n-octadecylmercaptopropionyl chloride,
n-hexylmercaptoacetyl chloride,
1,5-dichlorocarbonyl-3-thiapentane (i.e., the diacid dichloride of mercaptodipropionic acid),
diethyl chlorophosphite,
diphenyl chlorophosphite,
2-[3-(3,5-di-t-butyl-4-hydroxyphenyl)propionyloxy]ethyl chloroformate,
2-[3-(3,5-di-t-butyl-4-hydroxyphenyl)propionyloxy]propyl chloroformate,
2-(3,5-di-t-butyl-4-hydroxybenzoyloxy)propyl chloroformate,
3,5-di-t-butyl-4-hydroxybenzyl chloroformate,
3-(3,5-di-t-butyl-4-hydroxybenzyloxycarbonyl)propionyl chloride and
4-(3,5-di-t-butyl-4-hydroxybenzyloxycarbonyl)butyryl chloride.

A number of reactive AO's are prepared by reacting the corresponding antioxidant acid with an acid halogenating agent, such as thionyl chloride, thionyl bromide, phosphorous trichloride, phosphorous pentachloride, phosgene (in the presence of catalysts such as N,N-dimethylformamide) and benzotrichloride, or by reacting the corresponding antioxidant alcohol (e.g., 2-[3-(3,5-di-t-butyl-4-hydroxyphenyl)propionyloxy]ethanol) with phosgene, followed by isolation of the antioxidant acid halide or chloroformate from the reaction mixture. These AO's with acid halide or chloroformate groups are co-reactive with t-alkyl hydroperoxide or peroxy compounds possessing hydroxy, amino or hydrazino groups. The hydroxy group on the phenyl ring of reactive hindered phenol antioxidants is relatively non-reactive with acid halide or chloroformate groups.

Co-reactive t-alkyl hydroperoxides include t-butyl hydroperoxide, t-amyl hydroperoxide, t-octyl hydroperoxides, t-decyl hydroperoxides, α-cumyl hydroperoxide, methyl-α-cumyl hydroperoxides, 2-naphthyl-2-hydroperoxypropane, 2,5-dimethyl-2,5-dihydroperoxyhexane, 2,5-dimethyl-2,5-dihydroperoxy- 3-hexyne and 2,5-dimethyl-2-(t-butylperoxy)- 5-hydroperoxyhexane.

Co-reactive peroxy compounds possessing hydroxy groups include the hydroxy dialkyl peroxides, such as those disclosed in U.S. Pat. No. 3,236,872, which are hereby incorporated herein by reference, such as 1,3-dimethyl-3-(t-butylperoxy)butanol, 1,3-dimethyl-3-(t-amyl-peroxy)butanol and di-(3-hydroxy-1,1-dimethylbutyl) peroxide. Other co-reactive hydroxy dialkyl peroxides include 1,3-dimethyl-3-(α-cumylperoxy)butanol, 3-methyl-3-(t-butyl-peroxy)butanol and di-(3-hydroxy-1,1-dimethylpropyl) peroxide.

Other co-reactive peroxy compounds possessing hydroxy groups include hydroxy peroxyesters, for example, those disclosed in U.S. Pat. No. 4,525,308, which are hereby incorporated herein by reference, such as 3-hydroxy-1,1-dimethylbutyl peroxy-2-ethylhexanoate.

Yet other co-reactive peroxy compounds possessing hydroxy groups include hydroxy diperoxyketals, such as 4-hydroxy-2,2-di-(t-butylperoxy)butane and 5-hydroxy-2,2-di-(t-amyl-peroxy)pentane.

Hydroxy hydroperoxides such as 3-hydroxy- 1,1-dimethylbutyl hydroperoxide and 3-hydroxy- 1,1-dimethylpropyl hydroperoxide are also co-reactive peroxy compound possessing hydroxy groups which react with AO's possessing acid halide or chloroformate groups to form peroxyesters having two AO groups per peroxyester group.

Hydrogen peroxide is also a co-reactive peroxy compound which reacts with AO's possessing acid halide or chloroformate groups to form diacyl peroxides possessing two AO groups per diacyl peroxide group.

Co-reactive peroxy compounds possessing amino groups include amino dialkyl peroxides and amino diperoxyketals that are prepared by reacting a peroxy acid chloride or chloroformate with excess alkylenediamine, for example ethylenediamine.

Co-reactive peroxy compounds possessing hydrazino groups include hydrazino dialkyl peroxides and hydrazino diperoxyketals that are prepared by reacting peroxy acid chlorides or chloroformates with excess hydrazine or by reacting a peroxy compound possessing an ester group with excess hydrazine.

Non-limiting examples of amino and hydrazino peroxides that are co-reactive with AO's possessing acid halide or chloroformate groups include compounds such as O-[1,3-dimethyl-3-(t-butylperoxy)butyl] N-(2-aminoethyl)carbamate, 4,4-di-(t-butylperoxy)pentanoylhydrazine, 3,3-di-(t-butylperoxy)butanoylhydrazine and 1,3-dimethyl- 3-(t-butylperoxy)butyl carbazate.

Non-limiting examples of AO's possessing hydroxy groups which are reactive with peroxy compounds possessing co-reactive acid halide or chloroformate groups include 2-(3-(3,5-di-t-butyl- 4-hydroxyphenyl)propionyloxy-)ethanol, 2-(3,5-di-t-butyl- 4-hydroxybenzoyloxy)propanol and 3,5-di-t-butyl- 4-hydroxybenzyl alcohol (also known as 4-hydroxymethyl- 2,6-di-t-butylphenol).

Peroxy compounds possessing co-reactive acid halide or chloroformate groups which are reactive with AO's possessing hydroxy groups include peroxyesters, such as t-butyl peroxy-(2-chlorocarbonyl)benzoate and t-butyl peroxy-(3-chlorocarbonyl)propionate, dialkyl peroxides such as 1,3-dimethyl-3-(t-butylperoxy)butyl chloroformate, di-(3-chlorocarbonyloxy-1,1-dimethylbutyl) peroxide and 3-methyl-3-(t-butylperoxy)butyl chloroformate, and diperoxyketals, such as 4,4-di-(t-butylperoxy)pentanoyl chloride.

Non-limiting examples of novel AO-P's (structure A) of this invention are as follows:
di-(3,5-di-t-butyl-4-hydroxybenzoyl) peroxide
di-[3-(3,5-di-t-butyl-4-hydroxyphenyl)propionyl] peroxide
t-butyl peroxy-(3,5-di-t-butyl-4-hydroxy)benzoate
t-amyl peroxy-(3,5-di-t-butyl-4-hydroxy)benzoate
t-octyl peroxy-(3,5-di-t-butyl-4-hydroxy)benzoate
t-butyl peroxy-3-(3,5-di-t-butyl-4-hydroxyphenyl)propionate
t-amyl peroxy-3-(3,5-di-t-butyl-4-hydroxyphenyl)propionate
t-decyl peroxy-3-(3,5-di-t-butyl-4-hydroxyphenyl)propionate
α-cumyl peroxy-3-(3,5-di-t-butyl-4-hydroxyphenyl)propionate
2,5-dimethyl-2,5-di-(3,5-di-t-butyl-4-hydroxybenzoylperoxy)hexane
2,5-dimethyl-2,5-di-(3,5-di-t-butyl-4-hydroxybenzoylperoxy)-3-hexyne
2,5-dimethyl-2,5-di-[3-(3,5-di-t-butyl-4-hydroxyphenyl)propionylperoxy]hexane
2,5-dimethyl-2,5-di-[3-(3,5-di-t-butyl- 4-hydroxyphenyl)propionylperoxy]-3-hexyne
2,5-dimethyl-2-(t-butylperoxy)-5-[3-( 3,5-di-t-butyl-4-hydroxyphenyl)propionylperoxy]-hexane
3-(3,5-di-t-butyl-4-hydroxybenzoyloxy)- 1,1-dimethylbutyl peroxy-(3,5-di-t-butyl-4-hydroxy)benzoate
3-[3-(3,5-di-t-butyl-4-hydroxyphenyl)-propionyloxy]- 1,1-dimethylbutyl peroxy-[3-(3,5-di-t-butyl- 4-hydroxyphenyl)]propionate
1,3-dimethyl-3-(2-ethylhexanoylperoxy)butyl (3,5-di-t-butyl-4-hydroxy)benzoate
3-methyl-3-(2-ethylhexanoylperoxy)butyl (3,5-di-t-butyl-4-hydroxy)benzoate
1,3-dimethyl-3-(neoheptanoylperoxy)butyl-( 3-(3,5-di-t-butyl-4-hydroxyphenyl)propionate
1,3-dimethyl-3-(neodecanoylperoxy)butyl 3-(3,5-di-t-butyl-4-hydroxyphenyl)propionate
OO-t-butyl O-(2-[3-(3,5-di-t-butyl- 4-hydroxyphenyl)propionyloxy]ethyl) monoperoxyphthalate
OO-t-amyl O-(2-(3,5-di-t-butyl-4-hydroxybenzoyloxy)propyl) monoperoxysuccinate
di-[3-(3,5-di-t-butyl-4-hydroxybenzoyloxy)- 1,1-dimethylbutyl] peroxide
di-(3-[3-(3,5-di-t-butyl-4-hydroxyphenyl)propionyloxy]-1,1-dimethylbutyl) peroxide
di-(3-[3-(3,5-di-t-butyl-4-hydroxyphenyl)propionyloxy]-1,1-dimethylpropyl) peroxide
1,3-dimethyl-3-(t-butylperoxy)butyl (3,5-di-t-butyl-4-hydroxy)benzoate
3-methyl-3-(t-butylperoxy)butyl (3,5-di-t-butyl- 4-hydroxy)benzoate
1,3-dimethyl-3-(t-butylperoxy)butyl 3-( 3,5-di-t-butyl-4-hydroxyphenyl)propionate
3-methyl-3-(t-butylperoxy)butyl 3-(3,5-di-t-butyl- 4-hydroxyphenyl)propionate
4,4-di-(t-butylperoxy)pentyl 3-(3,5-di-t-butyl- 4-hydroxyphenyl)propionate
2-[3-(3,5-di-t-butyl-4-hydroxyphenyl)-propionyloxy] ethyl 1,3-dimethyl-3-(t-butylperoxy)butyl carbonate
2-(3-(3,5-di-t-butyl-4-hydroxyphenyl)propionyloxy)propyl 3-methyl-3-(t-butylperoxy)butyl carbonate
2-(3-(3,5-di-t-butyl-4-hydroxyphenyl)propionyloxy)ethyl 4,4-di-(t-butylperoxy)pentanoate
t-butyl peroxy-(3-n-hexylmercapto)propionate
t-amyl peroxy-(3-n-dodecylmercapto)propionate
t-octyl peroxy-(2-methylmercapto)acetate
2,5-dimethyl-2,5-di-(3-n-hexylmercaptopropionylperoxy)hexane
2,5-dimethyl-2,5-di-(3-n-dodecylmercaptopropionylperoxy)- 3-hexyne
2,5-dimethyl-2-(t-butylperoxy)-5-(3-n-hexylmercaptopropionylperoxy)hexane
3-(3-n-hexylmercaptopropionyloxy)-1,1-dimethylbutyl peroxy-(3-n-hexylmercapto)propionate
3-(3-n-hexylmercaptopropionyloxy)-1,1-dimethylpropyl peroxy-(3-n-hexylmercapto)propionate
1,3-dimethyl-3-(t-butylperoxy)butyl 3-n-hexylmercaptopropionate
1,1-dimethyl-3-(3-hexylmercaptopropionyloxy)butyl peroxy-2-ethylhexanoate
3-methyl-3-(t-butylperoxy)butyl 3-n-hexylmercaptopropionate di-[(3-n-hexylmercaptopropionyloxy)-1,1-dimethylbutyl] peroxide di-[(3-n-hexylmercaptopropionyloxy)-1,1-dimethylpropyl] peroxide 4,4-di-(t-butylperoxy)pentyl 3-n-hexylmercaptopropionate 1,5-di-(t-butylperoxycarbonyl)-3-thiapentane 1,5-di-(t-octylperoxycarbonyl)-3-thiapentane 1,5-di-[4-(t-butylperoxy)-1,1,4,4-tetramethylbutylperoxycarbonyl]- 3-thiapentane 1,5-di-[1,3-dimethyl-3-(t-butylperoxy)-butoxycarbonyl]-3-thiapentane 1,5-di-[3-methyl-3-(t-butylperoxy)-butoxycarbonyl]-3-thiapentane 1,1-dimethyl-3-(diethoxyphosphinoxy)-butyl peroxy-2-ethylhexanoate 3-methyl-3-(t-butylperoxy)butyl diphenyl phosphite 1-(3,5-di-t-butyl-4-hydroxybenzoyl)-2-[ 4,4-di-(t-butylperoxy)pentanoyl]hydrazine 1-(3,5-di-t-butyl-4-hydroxybenzoyl)-2-[ 4,4-di-(t-amylperoxy)pentanoyl]hydrazine 1-[3-(3,5-di-t-butyl-4-hydroxyphenyl)propionyl]- 2-(4,4-di-(t-butylperoxy)pentanoyl)hydrazine 1-(3-(3,5-di-t-butyl-4-hydroxyphenyl)propionyl)- 2-(3,3-di-(t-butylperoxy)butanoyl)hydrazine 1-(3-n-hexylmercaptopropionyl)-2-[4,4-di-(t-butylperoxy)pentanoyl] hydrazine 1-[3-(3,5-di-t-butyl-4-hydroxyphenyl)-propionyl]- 2-[1,3-dimethyl-3-(t-butylperoxy)butoxycarbonyl] hydrazine N-[3-(3,5-di-t-butyl-4-hydroxyphenyl)propionyl]-N'-[ 1,3-dimethyl-3-(t-butylperoxy)butoxycarbonyl]ethylenediamine N-[1-methyl-1-(3-[1-(t-butylperoxy)-1-methylethyl] phenyl]ethyl]-3-(3,5-di-t-butyl-4-hydroxyphenyl)propanamide N-[1-methyl-1-(4-[1-(t-butylperoxy)-1-methylethyl)] phenyl]ethyl]-3-(3,5-di-t-butyl-4-hydroxyphenyl)propanamide 2,2'-(4-thia-1,7-heptanedioyl)bis[1,3-dimethyl- 3-(t-butylperoxy)butyl carbazate)]

1,3-dimethyl-3-(t-butylperoxy)butyl 3,5-di-t-butyl- 4-hydroxybenzyl carbonate 1,3-dimethyl-3-(2-ethylhexanoylperoxy)butyl 3,5-di-t-butyl-4-hydroxybenzyl carbonate t-butyl peroxy-3-(3,5-di-t-butyl-4-hydroxybenzyloxycarbonyl)propionate di-3-(3,5-di-t-butyl-4-hydroxybenzyloxycarbonyl)propionyl peroxide 1-[3-(3,5-di-t-butyl-4-hydroxyphenyl)propionyl]- 2-(3-t-butylperoxycarbonyl)propionylhydrazine 1-[3-(3,5-di-t-butyl-4-hydroxyphenyl)propionyl]- 2-(2-t-butylperoxycarbonyl)benzoylhydrazine.

Polymerization of Ethylenically Unsaturated Monomers

The novel AO-P's of structure A of this invention were found to be effective initiators with respect to efficiency (reduced initiator requirements, etc.) in the free radical polymerizations of ethylenically unsaturated monomers at suitable temperatures and pressures. In addition, the resulting polymeric resins had enhanced oxidative stabilities owing to covalent attachment of the AO moieties from the AO-P's to the polymer backbone.

Suitable ethylenically unsaturated monomers which can be polymerized and copolymerized effectively using the AO-P's of the present invention include the following, non-limiting types: olefins, such as ethylene, propylene, styrene, α-methylstyrene, p-methylstyrene, chlorostyrenes, bromostyrenes, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid and methacrylic acid and their anhydrides, esters and amides, such as acrylic acid anhydride, methyl, ethyl, n-butyl, 2-hydroxyethyl, lauryl and 2-ethylhexyl acrylates and methacrylates, and acrylamide and methacrylamide; maleic anhydride and itaconic anhydride; maleic, itaconic and fumaric acids and their esters; vinyl halo and vinylidene dihalo compounds, such as vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, allyl ethyl carbonate, triallyl phosphate, diallyl phthalate, diallyl fumarate, diallyl glutarate, diallyl adipate, diallyl carbonate, diethylene glycol bis(allyl carbonate) (i.e., ADC); acrolein; methyl vinyl ketone; and mixtures thereof.

Temperatures of about 0° C. to about 250° C., preferably about 30° C. to about 200° C., and AO-P levels (on a pure basis) of about 0.002 to about 3%, preferably about 0.002 to about 1% by weight based on monomer, are normally employed in conventional polymerizations and copolymerizations of ethylenically unsaturated monomers and may be used with the polymerization and copolymerization processes of the present invention. The AO-P's of this invention can be used in combination with other free radical initiators such as those disclosed in the paragraph between columns 4 and 5 of U.S. Pat. No. 4,525,308. Using the AO-P's in combination with these initiators adds flexibility to the processes of polymer producers and allows them to "fine tune" their polymerization processes. Mixtures of two or more AO-P's can also be used where appropriate.

Curing of Unsaturated Polyester Resins

In the curing of unsaturated polyester resin compositions by heating at suitable curing temperatures in the presence of free radical curing agents, the AO-P's of structure A of this invention exhibit curing activity and enhance the oxidative stabilities of the cured unsaturated polyester resin compositions. Unsaturated polyester resins that can be cured by the AO-P's of this invention usually include an unsaturated polyester and one or more ethylenically unsaturated monomers.

The unsaturated polyesters are, for instance, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, for example, with saturated and unsaturated di- or polyols, such as ethylene glycol, diethylene glycol, triethylene glycol, 1,2- and 1,3-propanediols, 1,2-, 1,3- and 1,4-butanediols, 2,2-dimethyl-1,3-propanediol, 2-hydroxymethyl- 2-methyl-1,3-propanediol, 2-buten- 1,4-diol, 2-butyn-1,4-diol, 2,4,4-trimethyl-1,3-pentanediol, glycerol, pentaerythritol, mannitol and others. Mixtures of such di- or polyacids and/or mixtures of such di- or polyols may also be used.

The di- or polycarboxylic acids may be partially replaced by saturated di- or polycarboxylic acids, such as adipic acid, succinic acid, sebacic acid and other, and/or by aromatic dior polycarboxylic acids, such as phthalic acid, trimellitic acid, pyromellitic acid, isophthalic acid and terephthalic acid. The acids used may be substituted by groups such as halogen. Examples of such suitable halogenated acids are, for instance, tetrachlorophthalic acid, tetrabromophthalic acid, 5,6-dicarboxy-1,2,3,4,7,7-hexachlorobicyclo-( 2.2.1)-2-heptene and others.

The other component of the unsaturated polyester resin composition, the polymerizable monomer or monomers, preferably includes ethylenically unsaturated monomers, such as styrene, α-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl acrylate, n-butyl methacrylate, ethyl acrylate, and others, or mixtures thereof, which are copolymerizable with the unsaturated polyesters.

A preferred unsaturated polyester resin composition contains as the unsaturated polyester component the esterification product of 1,2-propanediol (a polyol), maleic anhydride (an anhydride of an unsaturated polycarboxylic acid) and phthalic anhydride (an anhydride of an aromatic dicarboxylic acid), as well as the monomer component, styrene.

Other types of unsaturated polyester resin compositions can be cured using the AO-P's of this invention as curing catalysts. These resins, called unsaturated vinyl ester resins, comprise a vinyl ester resin portion and one or more polymerizable monomer components. The vinyl ester resin component can be made by reacting a chloroepoxide, such as epichlorohydrin, with appropriate amounts of a bisphenol such as Bisphenol A (2,2-(4-hydroxyphenyl)propane), in the presence of a base, such as sodium hydroxide, to yield a condensation product having terminal epoxy groups derived from the chloroepoxide. Subsequent reaction of the condensation product with polymerizable unsaturated carboxylic acids, such as acrylic acid and methacrylic acid, in the presence or absence of acidic or basic catalysts, results in formation of the vinyl ester resin component. Normally, styrene is added as the polymerizable monomer component to complete the preparation of the unsaturated vinyl ester resin composition.

Temperatures of about 20° C. to about 200° C. and AO-P levels of about 0.05% to about 5% or more by weight of curable unsaturated polyester resin composition are normally employed.

The unsaturated polyester resin compositions described above can be filled with various materials, such as sulfur, glass, carbon and boron fibers, carbon blacks, silicas, metal silicates, clays, metal carbonates, other antioxidants (AO's), heat, ultraviolet (UV) and light stabilizers, sensitizers, dyes, pigments, accelerators, metal oxides, such as zinc oxide, blowing agents, nucleating agents and others.

Curing of Elastomers and Crosslinking of Thermoplastic Polymers

In the curing of elastomeric compositions, and the crosslinking of polymer compositions, by heating at suitable curing and crosslinking temperatures in the presence of free radical curing and crosslinking agents, the AO-P's of structure A of this invention exhibit curing and crosslinking activities, and enhance the oxidative stabilities of the cured elastomeric resin compositions and of the crosslinked polymer compositions.

Elastomeric resin compositions that can be cured by the AO-P's of this invention include elastomers such as ethylene-propylene copolymers (EPR), ethylene-propylene-diene terpolymers (EPDM), polybutadiene (PBD), silicone rubber (SR), nitrile rubber (NR), neoprene, fluoroelastomers and ethylene-vinyl acetate copolymer (EVA).

Polymer compositions that can be crosslinked by the AO-P's of this invention include olefin thermoplastics such as chlorinated polyethylene (CPE), low density polyethylene (LDPE), linear low density polyethylene (LLDPE), and high density polyethylene (HDPE). Other crosslinkable thermoplastic polymers include PVC, polystyrene, poly(vinyl acetate), polyacrylics, polyesters, polycarbonate, etc.

Temperatures of about 80° C. to about 310° C. and AO-P levels of about 0.1% to about 10%, preferably about 0.5% to about 5%, based on weight of curable elastomeric resin composition or crosslinkable olefin polymer composition, are normally employed.

The curable elastomeric resin composition or crosslinkable polymer composition can be optionally filled with the materials listed above for use with the conventional unsaturated polyester resin compositions.

Modification of Polyolefins and Other Polymers

In the processes for modifying polypropylene (PP) (i.e., beneficial degradation of PP by reducing the polymer molecular weight and modifying the polymer molecular weight distribution as judged by melt flow index increase and melt viscosity decrease) and copolymers containing more than 50% by weight of polypropylene, the AO-P's of structure A of this invention exhibit PP modification activity and concomitant enhancement of the oxidative stability of modified PP resin compositions. Other polymers that can be modified with AO-P's of. structure A include low density polyethylene (LDPE), linear low density polyethylene (LLDPE), high density polyethylene (HDPE), etc. Unlike modification of PP and propylene copolymers, modification of these other polymers with the AO-P's of structure A usually results in chain extension, melt flow index reduction, melt viscosity increase and molecular weight increase.

Temperatures of about 140° C. to about 340° C. and AO-P levels of about 0.01% to about 1.0% based on weight of modifiable PP, propylene copolymer or other polymers are normally employed. Optionally, up to 1% by weight of molecular oxygen can be employed as a modification co-catalyst.

The following illustrative, non-limiting examples are included for the purpose of further describing and explaining the invention.

EXAMPLE 1

Preparation of t-butyl peroxy-3-(3,5-di-t-butyl-4-hydroxyphenyl)propionate otherwise known by its IUPAC name, t-butyl 3-(3,5-di-t-butyl-4-hydroxyphenyl)peroxypropionate (E-1)

A 300 ml 3-neck flask equipped with a magnetic stirring bar, a thermometer, a condenser and an addition funnel, was charged with 4.6 g (0.05 mole) of 97% t-butyl hydroperoxide, 5.5 g (0.07 mole) of pyridine and 50 ml of methylene chloride. To this vigorously stirred solution at 20°–25° C. was added a solution of 10.2 g (0.033 mole) of 98% 3-(3,5-di-t-butyl-4-hydroxyphenyl)propionylchloride (prepared by reacting 3-(3,5-di-t-butyl-4-hydroxyphenyl)propionic acid with thionyl chloride in the presence of a small amount of dimethylformamide) in 50 ml of methylene chloride over a period of 30 minutes. The resulting mixture was then stirred for 180 minutes at 25°–30° C., then washed in turn at 15°–20° C. with 75 ml (0.105 mole) of 5% aqueous HCl, 50 g of a solution consisting of 40 g of water, 5 g (0.040 mole) of sodium sulfite, 3 g (0.037 mole) of sodium acetate and 2 g (0.033 mole) of acetic acid, and 50 g of 8% aqueous sodium hydrogen carbonate solution. After each wash the aqueous phase was separated from the methylene chloride solution and discarded. In the case of the last wash an emulsion resulted which was broken by adding 10% aqueous sodium acetate solution (ca. 50 ml). The methylene chloride solution was given a final 50 g 10% aqueous sodium sulfate wash. The resulting methylene chloride solution was dried over about 5% by weight of anhydrous magnesium sulfate, and, after separation of the spent desiccant by filtration, the methylene chloride was removed in vacuo at 15–20 torr. using a rotatory evaporator at aspirator pressure.

9.4 g (81% uncorrected yield) of a yellow liquid product having a peroxyester active oxygen content of 3.83% was obtained. The assay of the product based on the active oxygen content was 83.9% and the corrected yield was 68%. An infrared (IR) spectrum of the product showed a strong hindered phenolic OH band at about 3650 cm$^{-1}$, a strong peroxyester carbonyl band at about 1790 cm$^{-1}$ and a strong peroxide (—OO—) band at about 840 cm$^{-1}$. A DSC scan showed a peroxide decomposition exotherm centered at a temperature of 166° C., thus confirming the presence of the peroxyester function in the product. These data confirmed the structure of the title compound.

EXAMPLE 2

Preparation of 1,3-dimethyl-3-(t-butylperoxy)butyl (3,5-di-t-butyl-4-hydroxy)benzoate otherwise known by its IUPAC name, 1,3-dimethyl-3-(t-butyldioxy)butyl 3,5-di-t-butyl-4-hydroxybenzoate (E-2)

A jacketed reactor equipped with an efficient mechanical stirrer, a thermometer and a dropping funnel was charged with 5.1 g (0.025 mole) of 94% 1,3-dimethyl-3-(t-butylperoxy)butanol, 5 g (0.063 mole) of pyridine, 0.2 g (0.0016 mole) of 4-(N,N-dimethylamino)pyridine (DMAP) and 75 ml of methylene chloride. To the resulting, vigorously stirred solution at 20°–25° C. was added a solution of 6.8 g (0.025 mole) of 99.2% 3,5-di-t-butyl- 4-hydroxybenzoyl chloride (prepared by reacting 3,5-di-t-butyl- 4-hydroxyphenylbenzoic acid with thionyl chloride in the presence of a small amount of dimethylformamide) in 75 ml of methylene chloride over a period of 15 minutes. The resulting solution was stirred at 20°–25° C. for 90 minutes, then washed in turn at 15°–20° C. with two 50 ml portions of 1.5M aqueous HCl solution, then with two 50 g portions of 14% aqueous ammonia solution. The resulting methylene chloride solution was dried over about 10% by weight of anhydrous magnesium sulfate, and, after separation of the spent desiccant by filtration, the methylene chloride was removed in vacuo at 15–20 torr. using a rotatory evaporator at aspirator pressure.

A liquid that contained solids was obtained. Pentane was added and additional solids formed. These were removed by filtration and the pentane was removed in vacuo leaving 8.6 g (81% uncorrected yield) of a yellow oil. An IR spectrum of the product showed that it consisted of the desired product as well as 1,3-dimethyl-3-(t-butylperoxy)butanol, one of the starting reactants.

The product was dissolved in 25 ml of pentane and a stoppered container with this solution was placed in a dry ice chest to encourage crystallization. The pentane mother liquor was decanted from the solid and taken up in an additional 25 ml of pentane. This solution was dried over anhydrous magnesium sulfate, and, after separation of the spent desiccant by filtration, the pentane was removed in vacuo. 2.6 g (25% uncorrected yield) of a yellow solid was obtained, m.p. 61°–64° C. An IR spectrum of the product showed a strong hindered phenolic OH band at about 3610 cm$^{-1}$, a strong ester carbonyl band at about 1700 cm$^{-1}$ and a peroxide (—OO—) band at about 870 cm$^{-1}$. A DSC scan showed a peroxide decomposition exotherm centered at a temperature of 201° C., thus confirming the presence of the dialkyl peroxide function in the product. These data confirmed the structure of the title compound.

EXAMPLE 3

Preparation of 3-methyl-3-(t-butylperoxy)butyl (3,5-di-t-butyl-4-hydroxy)benzoate otherwise known by its IUPAC name, 3-methyl-3-(t-butyldioxy)butyl 3,5-di-t-butyl-4-hydroxyenzoate (E-3)

A jacketed reactor equipped with an efficient mechanical stirrer, a thermometer and a dropping funnel was charged with 5.1 g (0.025 mole) of 87% 3-methyl-3-(t-butylperoxy)butanol, 5 g (0.063 mole) of pyridine, 0.2 g (0.0016 mole) of 4-(N,N-dimethylamino)pyridine (DMAP) and 75 ml of methylene chloride. To the resulting, vigorously stirred solution at 20°–25° C. was added a solution of 6.8 g (0.025 mole) of 99.2% 3,5-di-t-butyl-4-hydroxybenzoyl chloride in 75 ml of methylene chloride over a period of 15 minutes. The resulting solution was stirred at 20°–25° C. for 180 minutes, then washed in turn at 15°–20° C. with two 50 ml portions of 1.5M aqueous HCl solution, then with 50 ml portions of water to neutral. The resulting methylene chloride solution was dried over about 10% by weight of anhydrous magnesium sulfate, and, after separation of the spent desiccant by filtration, the methylene chloride was removed in vacuo.

The resulting product was 10.1 g (98% uncorrected yield) of a heavy yellow oil. An IR spectrum of the product showed a strong hindered phenolic OH band at about 3610 cm$^{-1}$, a minor OH band at 3550 cm$^{-1}$, a strong ester carbonyl band at about 1700 cm$^{-1}$ and a peroxide (—OO—) band at about 880 cm$^{-1}$. A DSC scan showed a peroxide decomposition exotherm centered at a temperature of 202° C., thus confirming the presence of the dialkyl peroxide function in the product. These data confirmed the structure of the title compound.

EXAMPLE 4

Preparation of 1,3-dimethyl-3-(t-butylperoxy)butyl (3,5-di-t-butyl-4-hydroxyphenyl)propionate otherwise known by its IUPAC name, 1,3-dimethyl-3-(t-butyldioxy)butyl 3-(3,5-di-t-butyl-4-hydroxyphenyl)propionate (E-4)

A 3-neck, round bottom flask equipped with an efficient mechanical stirrer, a thermometer and a dropping funnel was placed in a cooling bath and was charged with 2.6 g (0.0127 mole) of 93% 1,3-dimethyl-3-(t-butylperoxy)butanol, 2.6 g (0.033 mole) of pyridine and 100 g of methylene chloride. To the resulting, vigorously stirred solution at −5° to 0° C. was added a solution of 3.8 g (0.0127 mole) of 100%

3-(3,5-di-t-butyl-4-hydroxyphenyl)propionyl chloride in 40 g of methylene chloride over a period of 10 minutes. The resulting solution was allowed to stir at 0°–2° C. for 60 minutes, then washed in turn at 15°–20° C. with two 50 g portions of 5% aqueous HCl solution, then with a 50 g portion of 3% aqueous sodium hydrogen carbonate solution. The resulting methylene chloride solution was dried over about 10 g by weight of anhydrous magnesium sulfate, and, after separation of the spent desiccant by filtration, the methylene chloride was removed in vacuo leaving 5.6 g (98% uncorrected yield) of a viscous yellow liquid. An IR spectrum of the product showed a strong hindered phenolic OH band at about 3610 $cm^{-1}$, an ester carbonyl band at about 1730 $cm^{-1}$ and a peroxide (—OO—) band at about 870 $cm^{-1}$. These data indicate that the desired product was obtained.

EXAMPLE 5

Preparation of 3-methyl-3-(t-butylperoxy)butyl
(3,5-di-t-butyl-4-hydroxyphenyl)propionate
otherwise known by its IUPAC name,
3-methyl-3-(t-butyldioxy)butyl
3-(3,5-di-t-butyl-4-hydroxyphenyl)propionate (E-5)

A jacketed reactor equipped with an efficient mechanical stirrer, a thermometer and a dropping funnel was charged with 2.6 g (0.0127 mole) of 87% 3-methyl-3-(t-butylperoxy)butanol, 2.5 g (0,032 mole) of pyridine and 75 ml of methylene chloride. To the resulting, vigorously stirred solution at 0°–5° C. was added a solution of 3.8 g (0.0127 mole) of 100% 3-(3,5-di-t-butyl-4-hydroxyphenyl)propionyl chloride in 25 ml of methylene chloride over a period of 5 minutes. The resulting solution was allowed to stir at 0°–5° C. or 60 minutes, then washed in turn at 15°–20° C. with two 50 ml portions of 1.5M aqueous HCl solution, then with a 50 ml portion of saturated aqueous sodium hydrogen carbonate solution. The resulting methylene chloride solution was dried over about 10% by weight of anhydrous magnesium sulfate, and, after separation of the spent desiccant by filtration, the methylene chloride was removed in vacuo leaving 5.6 g (100% uncorrected yield) of a bright yellow oil. An IR spectrum of the product showed a strong hindered phenolic OH band at about 3610 $cm^{-1}$, an ester carbonyl band at about 1730 $cm^{-1}$ and a peroxide (—OO—) band at about 870 $cm^{-1}$. These data indicate that the desired product was obtained.

EXAMPLE 6

Preparation of 1,3-dimethyl-3-(t-butylperoxy)butyl
3-n-hexylmercaptopropionate otherwise known by
its IUPAC name, 1,3-dimethyl-3-(t-butyldioxy)butyl
3-(n-hexylthio)propionate (E-6)

A jacketed reactor equipped with an efficient mechanical stirrer, a thermometer and a dropping funnel was charged with 4.1 g (0.020 mole) of 93% 1,3-dimethyl-3-(t-butylperoxy)butanol, 4.6 g (0.058 mole) of pyridine and 75 ml of methylene chloride. To the resulting, vigorously stirred solution at 20°–25° C. was added a solution of 5.2 g (0.025 mole) of 3-hexylmercaptopropionyl chloride (prepared in a two step reaction; Witco's Mark 2140, tetra-(3-hexylmercaptopropionyloxymethyl)methane, was hydrolyzed in methanolic KOH to the K-salt of 3-hexylmercaptopropionic acid, acidified to 3-hexylmercaptopropionic acid and the acid converted to the acid chloride by reacting with thionyl chloride in the presence of a small amount of dimethylformamide) in 25 ml of methylene chloride over a period of 4 minutes. The resulting solution was stirred at 20°–25° C. for 120 minutes, then washed in turn at 15°–20° C. with two 50 ml portions of 1.0M aqueous HCl solution, then with three 100 g portions of 5% aqueous NaOH solution, then with a 50 g portion of water, and finally with a 50 g portion of 33% aqueous sodium dihydrogen phosphate solution. The resulting brown methylene chloride solution was dried over about 10% by weight of anhydrous magnesium sulfate, and, after separation of the spent desiccant by filtration, the methylene chloride was removed in vacuo at 15– 20 torr. using a rotatory evaporator at aspirator pressure. 5.0 g (68.5% uncorrected yield) of a liquid product that had a low sulfur odor was produced. An FTIR spectrum of the product showed a minor OH band at about 3290 $cm^{-1}$, a strong ester carbonyl band at about 1735 $cm^{-1}$ and a peroxide (—OO—) band at about 875 $cm^{-1}$. A gas chromatogram (gc) of the product showed that it was contaminated with a small amount (about 12–13%) of 1,3-dimethyl- 3-(t-butylperoxy)butanol, one of the starting reactants.

EXAMPLE 7

Preparation of 1,1-dimethyl-3-(
3-hexylmercaptopropionyloxy)butyl
peroxy-2-ethylhexanoate otherwise known by its
IUPAC name,
1,1-dimethyl-3-[3-(n-hexylthio)propionyloxy]butyl
perioxy-2-ethylhexanoate (E-7)

A jacketed reactor equipped with an efficient mechanical stirrer, a thermometer and a dropping funnel was charged with 9.8 g (0.020 mole) of 53.1% 3-hydroxy-l,l-dimethylbutyl peroxy-2-ethylhexanoate in toluene, 3.6 g (0.045 mole) of pyridine and 75 ml of methylene chloride. To the resulting, vigorously stirred solution at 20°–25° C. was added a solution of 4.6 g (0.022 mole) of 3-hexylmercaptopropionyl chloride in 25 ml of methylene chloride over a period of 4 minutes. The resulting solution was stirred at 20°–25° C. for 150 minutes, then washed in turn at 15°–20° C. with two 50 ml portions of 1.0M aqueous HCl solution, then with two 100 g portions of 10% aqueous NaOH solution, then with water to neutral. The resulting methylene chloride-toluene solution was dried over about 10% by weight of anhydrous magnesium sulfate, and, after separation of the spent desiccant by filtration, the methylene chloride and toluene were removed in vacuo at 15–20 torr. using a rotatory evaporator at aspirator pressure.

6.5 g (75.6% uncorrected yield) of an amber liquid product that had a low sulfur odor was produced. An FTIR spectrum of the product showed a minor OH band at about 3270 $cm^{-1}$, a strong peroxyester carbonyl band at about 1775 $cm^{-1}$, a strong ester carbonyl band at about 1730 $cm^{-1}$ and a peroxide (—OO—) band at about 830 $cm^{-1}$. The active oxygen found for the product was 3.19% (theory, 3.70%), therefore, the assay of the product was 86.2% and the corrected yield was 65.2%.

EXAMPLE 8

Preparation of 1-(3,5-di-t-butyl-4-hydroxybenzoyl)-
2-[4,4-di-(t-butylperoxy)pentanoyl]hydrazine
otherwise known by its IUPAC name,
1-[4,4-di-(t-butyldioxy)pentano]-2-(3,5-di-t-butyl-
4-hydroxybenzo)hydrazide (E-8)

4,4-Di-(t-butylperoxy)pentanoylhydrazine was initially prepared by reacting ethyl 4,4-di-(t-butylperoxy)pentanoate with 9 molar excess of 54% aqueous hydrazine. A 3-neck flask equipped with a magnetic stirrer, a thermometer and an addition funnel was charged with 125 ml of isopropanol (IPA), 15.3 g (0.05 mole) of 99% ethyl 4,4-di-(t-butylperoxy)pentanoate and 30 g (ca. 0.50 mole) of 54% aqueous hydrazine at 25° C. The solution was stirred for about 20 hours at 20°–25° C., then the reaction mass was poured into 1000 ml of water and extracted once with 300 ml of methylene chloride. After drying over 10% by weight of anhydrous magnesium sulfate and separation of the spent desiccant by filtration, the methylene chloride was removed in vacuo leaving 14.4 g of liquid product. 30 ml of pentane was added and a solid precipitated. The solid was separated by filtration and air dried, leaving 12.2 g (83.6% of theory, uncorrected) of a white solid, m.p., 76°–78° C. An IR spectrum of the product showed strong carbonyl absorption bands at 1640 $cm^{-1}$ and at 1680 $cm^{-1}$ and a strong NH band at 3300 $cm^{-1}$. A DSC scan run on the product showed a peroxide decomposition exotherm at 170° C. These product data confirm that the product was 4,4-di-(t-butylperoxy)pentanoylhydrazine.

The title product E-8 was prepared by the following procedure: A jacketed reactor equipped with an efficient mechanical stirrer, a dropping funnel and a thermometer was charged with 5.8 g (0.02 mole) of 4,4-di-(t-butylperoxy)pentanoylhydrazine (100% purity assumed), 4.0 g (0.051 mole) of pyridine and 60 ml of methylene chloride, and the resulting solution was cooled to 0° C. To this vigorously stirred solution at 0° C. was added a solution of 99.2% 3,5-di-t-butyl-4-hydroxybenzoyl chloride in 60 ml of methylene chloride over a period of 15 minutes. The reaction mixture was stirred an additional 90 minutes at 0° C., then allowed to warm to 20° C. over a period of an hour. The resulting solution was washed twice with 50 ml portions of 1N HCl solution, then with three (3) 100 ml portions of water. (The pH of the last wash was 7.) The methylene chloride solution was then dried over about 10% by weight of anhydrous magnesium sulfate. After separation of the spent desiccant by filtration the methylene chloride was removed in vacuo, leaving a solid/liquid slurry. The slurry was washed with pentane and the resulting white solid was separated by filtration and dried in a fume hood for a short period. 9.6 g (91.4% of theory, uncorrected) of white solid, m.p. 152°–154° C. was obtained. An IR spectrum of the product showed a very sharp and characteristic hindered phenolic OH absorption band at 3620 $cm^{-1}$, an NH band centered at about 3220 $cm^{-1}$, a carbonyl band at 1685 $cm^{-1}$, another carbonyl band at 1645 $cm^{-1}$ and an —OO— band at about 880 $cm^{-1}$. A DSC scan run on the product showed a peroxide decomposition exotherm at 180° C. These product data (IR spectral and DSC) as well as method of preparation confirm that the product was the desired title compound.

EXAMPLE 9

Preparation of 1-(3,5-di-t-butyl-4-hydroxybenzoyl)-2-[4,4-di-(t-amylperoxy)pentanoyl]hydrazine otherwise known by its IUPAC name,
1-[4,4-di-(t-amyldioxy)pentano]-2-(3,5-di-t-butyl-4-hydroxybenzo)hydrazide (E-9)

4,4-Di-(t-amylperoxy)pentanoylhydrazine was initially prepared by reacting ethyl 4,4-di-(t-amylperoxy)pentanoate with 9 molar excess of 54% aqueous hydrazine in a manner similar to that employed in Example 8 for the initial preparation of 4,4-di-(t-butylperoxy)pentanoylhydrazine. 4,4-di-(t-amylperoxy)pentanoylhydrazine had a DSC peroxide decomposition temperature of 171° C.

Using a procedure similar to that employed for preparation of the title compound of Example 8, the title compound of this example was prepared by reacting 3.2 g (0.01 mole) of 4,4-di-(t-amylperoxy)pentanoylhydrazine with 2.7 g (0.01 mole) of 99.2% 3,5-di-t-butyl-4-hydroxybenzoyl chloride in the presence of 2.0 g (0,026 mole) of pyridine and 120 ml of methylene chloride. 2.6 g (47% of theory, uncorrected) of white solid, mp 129°–131° C. was obtained. An IR spectrum of the product showed a very sharp and characteristic hindered phenolic OH absorption band at 3640 $cm^{-1}$, an NH band centered at about 3235 $cm^{-1}$, hydrazide carbonyl bands at 1695 $cm^{-1}$, 1675 $cm^{-1}$, 1660 $cm^{-1}$, and 1635 $cm^{-1}$ and a —OO— band at about 880 $cm^{-1}$. A DSC scan run on the product showed a peroxide decomposition exotherm at 176° C. These product data (IR spectral and DSC) as well as method of preparation confirm that the product was the desired title compound.

EXAMPLE 9A

Preparation of 1,3-dimethyl-3-(t-butyl-peroxylbutyl 3,5-di-t-butyl-4-hydroxybenzyl carbonate otherwise known by its IUPAC name,
3-methyl-3-(t-butyldioxy)butyl
3-(3,5-di-t-butyl-4-hydroxyphenyl)propionate
(E-9A)

A 250 ml 3-neck flask equipped with a magnetic stirring bar, a thermometer, a consenser with a $CaCl_2$ tube and an addition funnel, was charged with 75 ml of methyl t-butyl ether, 11.8 g (0.05 mole) of 3,5-di-t-butyl-4-hydroxybenzyl alcohol and 4.7 g (0.06 mole) of pyridine at 20°–25° C. To this vigorously stirred solution at 20°–25° C. was added 13.3 g (0.05 mole) of 95% 1,3-dimethyl- 3-(t-butylperoxy)butyl chloroformate over a period of 15 minutes at 20°–25° C. The resulting mixture was then stirred for 180 minutes at 25°–30° C. A solid formed during the stirring period. The solid was removed by filtration and the filtrate was washed at 20° C. twice with 50 ml portions of 5% aqueous $NaHCO_3$ solution, once with 50 ml of 33% aqueous $Na_2HPO_4$ solution and finally with 50 ml of 5% aqueous $NaHCO_3$ solution. The resulting solution was dried over about 5% by weight of anhydrous magnesium sulfate, and, after separation of the spent desiccant by filtration, the methyl t-butyl ether was removed in vacuo at 15–20 torr. using a rotatory evaporator at aspirator pressure. 22.8 g (101% uncorrected yield) of a yellow liquid product were obtained. An IR spectrum of the product showed a strong hindered phenolic OH band at about 3630 $cm^{-1}$ and a strong carbonate carbonyl band at about 1740 $cm^{-1}$. These data and the method of preparation confirmed that the product was the desired title compound (E-9A).

EXAMPLE 9B

Preparation of 1-[3-(3,5-di-t-butyl-4-hydroxyphenyl)propionyl]-2-(3-t-butylperoxycarbonyl)propionylhydrazine otherwise known by its IUPAC name,
1-[3-(t-butyldioxycarbonyl)propiono]-2-[3-(3,5-di-t-butyl-4-hydroxyphenyl)propiono]hydrazide
(E-9B)

A 500 ml 3-neck flask equipped with a magnetic stirring bar, a thermometer, a condenser with a $CaCl_2$ tube and an addition funnel, was charged with 200 ml of methyl t-butyl ether, 8.9 g (0.03 mole) of 99% 3-(3,5-di-t-butyl-4-hydroxyphenyl)propionic acid hydrazide and 5.1 g (0.05 mole) of triethylamine at 20°–25° C. To this vigorously stirred solution at 21°–26° C. was added 6.6 g (0.03 mole) of 95% 3-(t-butylperoxycarbonyl)propionyl chloride in about 10 ml of methyl t-butyl ether over a period of 15 minutes. The resulting mixture was then stirred for 240 minutes at 25°–30° C. A solid formed during the stir period and about 150 ml of additional methyl t-butyl ether was added to aid stirring. The reaction mass was then washed three times with 100 ml portions of water, twice with 100 ml portions of 33% aqueous Na2HPO$_4$ solution and finally twice with 100 ml portions of water. The resulting solution was dried over about 5% by weight of anhydrous magnesium sulfate, and, after separation of the spent desiccant by filtration, the methyl t-butyl ether was removed in vacuo at 15–20 torr. using a rotatory evaporator at aspirator pressure. A wet solid was obtained which was slurried with 100 ml of cold pentane and filtered to give 7.8 g (56% uncorrected yield) of a light tan solid, m.p. 147°–152° C. An IR spectrum of the product showed a hindered penolic OH band at about 3640 cm$^{-1}$, an NH band at about 3270 cm$^{-1}$ and a double carbonyl band at about 1705 cm$^{-1}$ and 1720 cm$^{-1}$. These data and the method of preparation confirmed that the product was the desired title compound (E-9B).

EXAMPLE 10

121° C. SPI Exotherms of t-butyl peroxy-3-(3,5-di-t-butyl-4-hydroxyphenyl)propionate otherwise known by its IUPAC name, t-butyl 3-(3,5-di-t-butyl-4-hydroxyphenyl)peroxypropionate (E-1)

The unsaturated polyester resin composition employed in this example was a mixture of an unsaturated polyester and styrene monomer. The unsaturated polyester was an alkyd resin made by esterifying the following components:

| Component | Quantity (moles) |
| --- | --- |
| Maleic Anhydride | 1.0 |
| Phthalic Anhydride | 1.0 |
| Propylene Glycol | 2.2 |

To the resulting resin was added 0.013% by weight of hydroquinone inhibitor. The alkyd resin had an Acid No. of 45–50. Seven (7) parts by weight of the above unsaturated polyester alkyd was diluted with three (3) parts by weight of monomeric styrene. The resulting unsaturated polyester resin composition had the following properties:
a. Viscosity (Brookfield No. 2 at 20 r.p.m.): 13.0 poise
b. Specific gravity: 1.14.

Gelation and cure characteristics of t-butylperbenzoate (A-1), a well known curing catalyst for unsaturated polyester resin compositions, and t-butyl peroxy-3-(3,5-di-t-butyl-4-hydroxyphenyl)propionate otherwise known by its IUPAC name, t-butyl 3-(3,5-di-t-butyl-4-hydroxyphenyl)peroxypropionate (E-1), an AO-P of the present invention, were determined using the Standard SPI Exotherm Procedure ("SPI Procedure for Running Exotherm Curves-Polyester Resins," published in the Preprint of the 16th Annual Conference—Reinforced Plastics Division, Society of the Plastics Industry, Inc., February, 1961). Using the procedure at 121° C. (250° F.) t-butyl perbenzoate (A-1) and E-1 were evaluated. The results are summarized in Table 10-1 and show that E-i, an AO-P of the instant invention, surprisingly cures the unsaturated polyester resin in spite of the presence of a free radical trapping hindered phenolic moiety in E-1.

TABLE 10-1

| | SPI Exotherm Data at 121° C. | | | | |
| --- | --- | --- | --- | --- | --- |
| Curing Catalyst | Level, % | Gel, mins | Cure, mins | Peak Exotherm, °C. | Barcol Hardness |
| A-1 | 1.0 | 3.0 | 3.9 | 420 | 45–50 |
| E-1 | 1.0 | 8.4 | 10.3 | 400 | 40–45 |

EXAMPLE 11

Polypropylene Modification with t-butyl peroxy-3-(3,5-di-t-butyl-4-hydroxyphenyl)propionate otherwise known by its IUPAC name, t-butyl 3-(3,5-di-t-butyl-4-hydroxphenyl)peroxypropionate (E-1)

A polypropylene (PP) base resin (Himont 6501) was used as the PP resin and t-butyl peroxy- 3-(3,5-di-t-butyl-4-hydroxy-phenyl)propionate otherwise known by its IUPAC name, t-butyl 3-(3,5-di-t-butyl- 4-hydroxyphenyl)peroxypropionate (E- 1), an AO-P of the present invention, was used as the modifying peroxide. PP with E-1 (0.357% by weight) and without E-1 were mixed in a C. W. Brabender Plasticorder at 180° C. for 5 minutes at 50 rpm. The PP compounds were then removed and the melt flow indices (MFI's) were determined according to ASTM Procedure D1238 under Condition 'L' (230° C., 2.16 Kg Load). The MFI results are summarized in Table 11-1 and show that E-1 does indeed modify PP as judged by the increased MFI of the E-1 modified PP compared to that of the control (i.e., 17.3 g/10 minutes vs. 7.4 g/10 minutes). The increased MFI meant that the melt viscosity of the E-1 modified PP decreased. In addition, the increased MFI indicated that the molecular weight of the PP was significantly decreased by modifying with E-1.

TABLE 11-1

| PP Compound | Modifier | Level, % | MFI, g/10 mins |
| --- | --- | --- | --- |
| Himont 6501 | None | 0.0 | 7.4 |
| Himont 6501 + E-1 | E-1 | 0.357 | 17.3 |

The above modified PP resins, as well as PP modified with 0.17% by wt of t-butyl perbenzoate (A-1), a prior art peroxide, were tested for oxidative stability using a Perkin Elmer Differential Scanning Calorimeter (DSC). Samples were placed in specimen pans open to an air purge. The temperature at the start was 40° C. with a heating rate of 20° C. per minute up to 170° C., then held at 170° C. for the rest of the test. During the test the heat flow to and from the sample was monitored. The relative oxidative stabilities of the resin samples was determined by the time required to obtain maximum heat flow from the test specimen. A long time means greater oxidative stability. Table 11-2 gives the times to maximum heat flow for the modified PP resin specimens.

TABLE 11-2

| DSC Oxidative Stability Modified PP Resin Compounds | |
|---|---|
| Peroxide Used for Modifying | Time to Max Heat from Resin, mins |
| None | 16 |
| A-1 | 15 |
| E-1 | 31 |

The results show that E-1, an AO-P of this invention, modifies PP and simultaneously gives a modified PP resin having oxidative stability significantly greater than PP modified without peroxide or modified with A-1, a prior art peroxide. The results indicate that antioxidant moieties derived from E-1 are covalently bonded to the modified PP resin compound.

EXAMPLE 12

Polybutadiene Curing with t-butyl peroxy-3-(3,5t-di-t-butyl-4-hydroxyphenyl) propionate otherwise known by its IUPAC name, t-butyl 3-(3,5-di-t-butyl-4-hydroxphenyl)peroxypropionate (E-1)

The resin employed was a mixture of 100 parts of Polysar's Taktene 1202 polybutadiene (PBD) elastomer and 50 parts of zinc diacrylate co-agent. Compositions such as PBD/Zn acrylate plus fillers are often cured to produce the main component of golf balls. With respect to the peroxide curing agent, either 1.0 part of t-butyl peroxy-3-(3,5-di-t-butyl- 4-hydroxyphenyl)propionate otherwise known by its IUPAC name, t-butyl 3-(3,5-di-t-butyl-4-hydroxyphenyl)peroxyproionate (E-1), or 0.48 part of t-butyl 4,4-di-(t-butylperoxy)valerate (A-2, Lucidol's Lupersol 230), a prior art curing agent for PBD, was used. The PBD/zinc diacrylate compounds were compounded in a Brabender Plastometer at room temperature for about three minutes. The compounds were then pressed out, cut into 10 gram disks and placed in a Monsanto Oscillating Disk Rheometer (ODR). The Monsanto ODR was operated at 160° C. with an arc of 1°. The torque and cure data obtained are summarized in Table 12-1.

TABLE 12-1

| 160° C. Rheometer Data Curing of PBD/Zn Diacrylate (2/1) Compound | | | | |
|---|---|---|---|---|
| Curing Agent | Mh, in-lbs | Mh–Ml, in-lbs | Tc90, mins | Ts2, mins |
| E-1 | 86 | 82 | 4.3 | 0.8 |
| A-2 | 134 | 130 | 2.6 | 0.6 |

M1= low torque in in-lbs.
Mh= high torque in in-lbs.
Mh-M1= Max. change in torque in in-lbs.
Tc90= time to 90% of cure in mins.
Ts2= scorch time in mins.

The results show that E-1 does cure the resin giving a rubbery and soft crosslinked composition. In comparison, use of A-2 produced a composition that was hard and brittle. The results obtained employing E-1 as the curing agent are desirable for a golf ball application, whereas the result obtained using A-2 as the curing agent are undesirable for a golf ball application.

The above cured resins were tested for oxidative stability using a Perkin Elmer Differential Scanning Calorimeter (DSC). Samples were placed in specimen pans open to an air purge. The temperature at the start was 40° C. with a heating rate of 20° C. per minute up to 170° C., then held at 170° C. for the rest of the test. During the test the heat flow to and from the sample was monitored. The relative oxidative stabilities of the resin samples were determined by the time required to obtain maximum heat flow from the test specimen. A long time means greater oxidative stability. Table 12-2 gives the times to maximum heat flow for the resin specimens.

TABLE 12-2

| DSC Oxidative Stability Cured PBD/Zn Diacrylate (2/1) Compounds | |
|---|---|
| Peroxide Used for Curing | Time to Max Heat from Resin, mins |
| E-1 | 38 |
| A-2 | 13 |

The results show that E-1 cures the PBD/Zn diacrylate compound to give a cured compound having oxidative stability significantly greater than PBD/Zn diacrylate cured with the prior art curing agent, A-2. The results indicate that antioxidant moieties derived from E-1 are covalently bonded to the cured resin compound.

The present invention may be embodied in other specific forms without departing from the spirit or essential attributes thereof and, accordingly, reference should be made to the appended claims, rather than to the foregoing specification as indicating the scope of the invention.

I claim:

1. An improved process for the modification of the molecular chain of a polymer wherein the process for modification is selected from among the group consisting of curing unsaturated polyester resin polymers, curing elastomeric resin polymers, crosslinking an olefin derived polymer and modifying the molecular weight and the molecular weight distribution of polymers selected from polypropylene, linear low density polyethylene, high density polyethylene and copolymers comprising more than 50% by weight of polypropylene which process comprises reacting the polymer with a peroxide in an amount and under conditions effective to initiate free radical formation from the peroxide and thereby initiate said modification of the molecular chain of said polymer wherein the improved process also enhances the oxidative stability of said polymer and consists of the incorporation in said process of an antioxidant-peroxide having structure A:

$$(Y-[-R-OO-X)_x-An]_y \qquad A$$

where x and y are 1 or 2, but when x is 2, y can only be 1, and when y is 2, x can only be 1 and with the following provisos (I), (II) and (III):

(I) when x is 1 and y is 1,

An is an antioxidant monoradical having a structure selected from the following structures (1), (2) and (3):

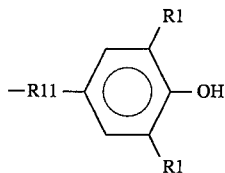

where

R1 is a t-alkyl radical of 4 to 8 carbons;

R11 is a structure selected from the group consisting of (a), (b), (c) and (d):

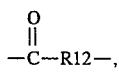

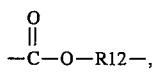

and

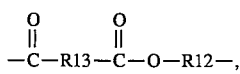

where R12 is selected from the group consisting of an alkylene diradical of 1 to 6 carbons and an alkenylene diradical of 2 to 6 carbons, and where R13 is selected from the group consisting of an alkylene diradical of 1 to 3 carbons, an unsubstituted 1,2-phenylene diradical, and a substituted 1,2-phenylene diradical, the substituents being selected from the group consisting of one or more lower alkyl radicals of 1 to 4 carbons, chloro, bromo, fluoro, carboxy and nitro;

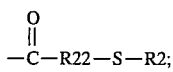

and

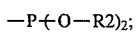

where

R2 is selected from the group consisting of an alkyl radical of 1 to 18 carbons and an aryl radical of 6 to 12 carbons, and R22 is selected from the group consisting of an alkylene diradical of 1 to 6 carbons and an alkenylene diradical of 2 to 6 carbons;

Y is nothing;

R is selected from the group consisting of a t-alkyl radical of 4 to 10 carbons, a t-aralkyl radical of 9 to 13 carbons, an acyl radical of 2 to 13 carbons, an aryl radical of 7 to 11 carbons, an alkoxycarbonyl radical of 2 to 13 carbons and the radical An—X—;

and

X is selected from the group consisting of a diradical (e), (f), (g), (h) and (i):

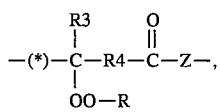

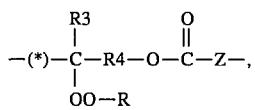

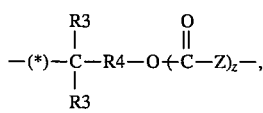

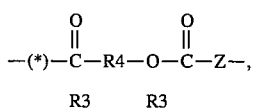

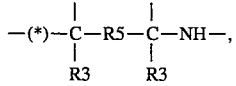

where the —(*)— shows the point of attachment of the —OO— grouping to the —X— diradical, the other end of the —X— diradical being attached to the An radical, when An is structure (1) and R11 is (b), (c) or (d), X is selected from the group consisting of a direct bond and a diradical (e), (f), (g), (h) and (i);

where

R3 is a lower alkyl radical of 1 to 4 carbons,

R4 is selected from the group consisting of an unsubstituted alkylene diradical of 2 to 4 carbons and a lower alkyl substituted alkylene diradical of 2 to 4 carbons, R5 is selected from the group consisting of an unsubstituted 1,3-phenylene diradical, an unsubstituted 1,4-phenylene diradical, a substituted 1,3-phenylene diradical and a substituted 1,4-phenylene diradical, the substituted R5 diradicals having substituents selected from the group consisting of lower alkyl, chloro or bromo, —Z— is the diradical

—NH—R6—NH—, where $R^6$ is selected from the group consisting of nothing, an unsubstituted alkylene diradical of 2 to 10 carbons, an unsubstituted 1,2-phenylene diradical, an unsubstituted 1,3-phenylene diradical, an unsubstituted 1,4-phenylene diradical, a substituted 1,2-phenylene diradical, a substituted 1,3-phenylene diradical and a substituted 1,4-phenylene diradical, the R6 substituted diradicals having substituents selected from the group consisting of lower alkyl, chloro and bromo; and z is 0 or 1;

(II) when x is 1 and y is 2,

An is an antioxidant monoradical having structure (4):

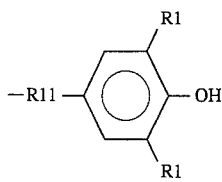

(4)

where
R1 is a t-alkyl radical of 4 to 8 carbons;
R11 is a structure selected from the group consisting of (j), (k) and (l):

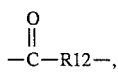

(j)

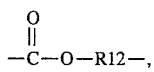

(k)

and

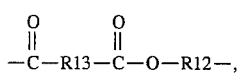

(l)

where
R12 and R13 are the same as when x is 1 and y is 1;
Y is selected from the group consisting of an alkylene diradical of 2 to 4 carbons and an ethynylene diradical;
X is a direct bond; and
R is the alkylide diradical

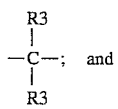

and (III) when x is 2 and y is 1;
an is an antioxidant diradical having the structure

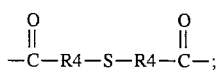

Y is nothing;
R is selected from the group consisting of a t-alkyl radical of 4 to 10 carbons, a t-aralkyl radical of 9 to 13 carbons, an acyl radical of 2 to 13 carbons, an aroyl radical of 7 to 11 carbons, and an alkyoxycarbonyl radical of 2 to 13 carbons; and
X is the same as when x is 1 and y is 1.

2. A process as defined in claim 1 wherein the antioxidant peroxide is selected from the group consisting of t-butyl 3-(3,5-di-t-butyl-4-hydroxyphenyl)peroxypropionate, 1,3-dimethyl- 3-(t-butyldioxy)butyl 3,5-di-t-butyl-4-hydroxybenzoate, 3-methyl-3-(t-butyldioxy)butyl 3,5-di-t-butyl-4-hydroxybenzoate, 1,3-dimethyl-3-(t-butyldioxy)butyl 3-(3,5-di-t-butyl-4-hydroxphenyl)propionate, 3-methyl-3-(t-butyldioxy)butyl 3-(3,5-di-t-butyl-4-hydroxyphenyl)propionate, 1-[4,4-di-(t-butyldioxy)pentano]-2-(3,5-di-t-butyl-4-hydroxybenzo)hydrazide, 1-[4,4-di-(t-amyldioxy)pentano]- 2-(3,5-di-t-butyl-4-hydroxybenzo)hydrazide, 3,5-di-t-butyl-4-hydroxybenzyl 1,3-dimethyl-3-(t-butyldioxy)butyl carbonate, and 1-[3-(t-butyldioxycarbonyl)propiono]-2-[ 3-(3,5-di-t-butyl-4-hydroxyphenyl)propiono]hydrazide.

3. A process as defined in claim 1 wherein the polymer is an unsaturated polyester resin polymer.

4. A process as defined in claim 2 wherein the polymer is an unsaturated polyester resin polymer.

5. A process as defined in claim 1 wherein the polymer is an elastomeric resin polymer.

6. A process as defined in claim 2 wherein the polymer is an elastomeric resin polymer.

7. A process as defined in claim 1 wherein the molecular weight is modified and the molecular weight distribution is modified for polymers selected from the group consisting of polypropylene, linear low density polyethylene, high density polyethylene and copolymers comprising more than 50% by weight of polypropylene.

8. A process as defined in claim 2 wherein the molecular weight is modified and the molecular weight distribution is modified for polymers selected from the group consisting of polypropylene, linear low density polyethylene and copolymers comprising more than 50% by weight of polypropylene.

9. A process as defined in claim 1 wherein an olefin derived polymer is cross-linked.

10. A process as defined in claim 2 wherein an olefin derived polymer is cross-linked.

11. An improved process for polymerizing an ethylenically unsaturated monomer comprising reacting said monomer with a peroxide in an amount and under conditions effective to initiate free radical formation from the peroxide, thereby initiating polymerization of the monomer, where the improved process also enhances the oxidation stabilty of the polymer, produced and consists of the incorporation in said process of an antioxidant-peroxide having structure A:

(Y—[—R—OO—X)$_x$—An]$_y$     A where
x and y are 1 or 2, but when x is 2, y can only be 1, and when y is 2, x can only be 1 and with the following provisos (I), (II) and (III):
(I) when x is 1 and y is 1,
an is an antioxidant monoradical having a structure selected from the following structures (1), (2) and (3):

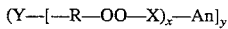

(1)

where
R1 is a t-alkyl radical of 4 to 8 carbons;
R11 is a structure selected from the group consisting of (a), (b), (c) and (d):

(a)

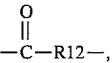

(b)

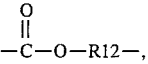

(c)

and

-continued

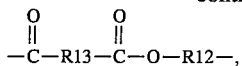 (d)

where
R12 is selected from the group consisting of an alkylene diradical of 1 to 6 carbons and an alkenylene diradical of 2 to 6 carbons, and where R13 is selected from the group consisting of an alkylene diradical of 1 to 3 carbons, an unsubstituted 1,2-phenylene diradical, and a substituted 1,2-phenylene diradical, the substituents being selected from the group consisting of one or more lower alkyl radicals of 1 to 4 carbons, chloro, bromo, fluoro, carboxy and nitro;

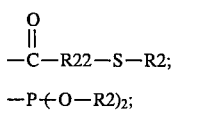

where
R2 is selected from the group consisting of an alkyl radical of 1 to 18 carbons and an aryl radical of 6 to 12 carbons, and
R22 is selected from the group consisting of an alkylene diradical of 1 to 6 carbons and an alkenylene diradical of 2 to 6 carbons;

Y is nothing;

R is selected from the group consisting of a t-alkyl radical of 4 to 10 carbons, a t-aralkyl radical of 9 to 13 carbons, an acyl radical of 2 to 13 carbons, an aroyl radical of 7 to 11 carbons, an alkoxycarbonyl radical of 2 to 13 carbons and the radical

and

X is selected from the group consisting of a diradical (e); (f), (g), (h) and (i):

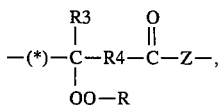

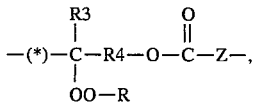

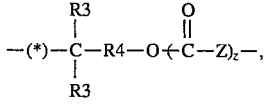

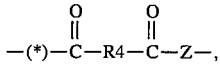

and,

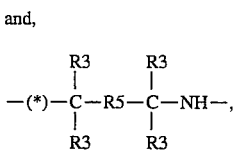

where the —(*)— shows the point of attachment of the —OO— grouping to the —X— diradical, the other end of the —X— diradical being attached to the An radical, when An is structure (1) and R11 is (b), (c) or (d), X is selected from the group consisting of a direct bond and a diradical (e), (f), (g), (h) and (i);

where
R3 is a lower alkyl radical of 1 to 4 carbons,
R4 is selected from the group consisting of an unsubstituted alkylene diradical of 2 to 4 carbons and a lower alkyl substituted alkylene diradical of 2 to 4 carbons,
R5 is selected from the group consisting of an unsubstituted 1,3-phenylene diradical, an unsubstituted 1,4-phenylene diradical, a substituted 1,3-phenylene diradical and a substituted 1,4-phenylene diradical the substituted R5 diradicals having substituents selected from the group consisting of lower alkyl, chloro or bromo, —Z— is the diradical

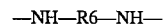

where
R6 is selected from the group consisting of nothing, an unsubstituted alkylene diradical of 2 to 10 carbons, an unsubstituted 1,2-phenylene diradical, an unsubstituted 1,3-phenylene diradical, an unsubstituted 1,4-phenylene diradical, a substituted 1,2-phenylene diradical, a substituted 1,3-phenylene diradical and a substituted 1,4-phenylene diradical, the R6 substituted diradicals having substituents selected from the group consisting of lower alkyl, chloro and bromo; and z is 0 to 1;

(II) when x is 1 and y is 2,
An is an antioxidant monoradical having structure (4):

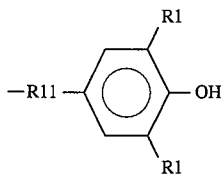

where
R1 is a t-alkyl radical of 4 to 8 carbons;
R11 is a structure selected from the group consisting of (j), (k) and (l):

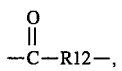

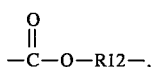

and

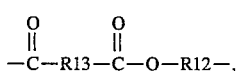

and where
R12 and R1 are the same as when x is 1 and y is 1;
Y is selected from the group consisting of an alkylene diradical of 2 to 4 carbons and an ethylene diradical;
X is a direct bond; and R is the alkylidene diradical

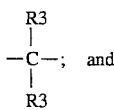

(III) when x is 2 and y is 1,

An is an antioxidant diradical having the structure

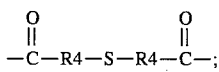

Y is nothing;

R is selected from the group consisting of a t-alkyl radical of 4 to 10 carbons, a t-aralkyl radical of 9 to 13 carbons, an acyl radical of 2 to 13 carbons, an aroyl radical of 7 to 11 carbons, and an alkoxycarbonyl radical of 2 to 13 carbons; and X is the same as when x is 1 and y is 1.

12. An improved process as defined in claim 10 wherein the antioxidant-peroxide is selected from the group consisting of:

t-butyl 3-(3,5-di-t-butyl-4-hydroxyphenyl)peroxypropionate, 1,3-dimethyl-3-(t-butyldioxy)butyl 3,5-di-t-butyl- 4-hydroxybenzoate, 3-methyl-3-(t-butyldioxy)butyl 3,5-di-t-butyl-4-hydroxybenzoate, 1,3-dimethyl-3-(t-butyldioxy)butyl 3-(3,5-di-t-butyl- 4-hydroxyphenyl)propionate, 3-methyl-3-t-butyldioxy)butyl-3-(3,5-di-t-butyl- 4-hydroxyphenyl)propionate, 1-[4,4-di-(t-butyldioxy)pentano]-2-(3,5-di-t-butyl- 4-hydroxybenzo)hydrazide, 1-[4,4-di-(t-amyldioxy)pentano]-2-(3,5-di-t-butyl- 4-hydroxybenzo)hydrazide, 3,5-di-t-butyl-4-hydroxybenzyl 1,3-dimethyl- 3-(t-butyldioxy)butyl carbonate, and 1-[3-(t-butyldioxycarbonyl)propiono]-2-( 3,5-di-t-butyl-4-hydroxyphenyl)propiono]hydrazide.

13. An improved process for polymerizing an ethylenically unsaturated monomer as defined in claim 11 wherein the monomer is styrene.

14. An improved process for polymerizing an ethylenically unsaturated monomer as defined in claim 12 wherein the monomer is styrene.

15. A polymer having enhanced oxidative stability made by the improved process defined in claim 11.

16. A polymer having enhanced oxidative stability made by the improved process defined in claim 12.

17. A polymer as defined in claim 15 wherein the monomer is selected from the group consisting of styrene, ethylene and vinyl chloride.

18. A polymer as defined in claim 16 wherein the monomer is selected from the group consisting of styrene, ethylene and vinyl chloride.

19. A cured polyester resin having enhanced oxidative stability made by the improved process defined in claim 1.

20. A cured polyester resin as defined in claim 19 wherein components of the cured resin are derived from unsaturated polyester and ethylenically unsaturated monomers.

21. A cured polyester resin having enhanced oxidative stability made by the process defined in claim 2.

22. A cured polyester resin as defined in claim 21 wherein the components of the cured resin are derived from unsaturated polyester and ethylenically unsaturated monomers.

23. A cured elastomeric resin having enhanced oxidative stability made by the process defined in claim 1.

24. A cured elastomeric resin as defined in claim 23 wherein the resin is selected from the group consisting of ethylene-propylene copolymers, ethylene-propylene-diene terpolymers, polybutadiene, silicone rubber, nitrile rubber, neoprene, fluoroelastomers and ethylene-vinyl acetate copolymer.

25. A cured elastomeric resin having enhanced oxidative stability made by the process of claim 2.

26. A cured elastomeric resin as defined in claim 25 wherein the resin is selected from the group consisting of ethylene-propylene copolymers, ethylene-propylene-diene terpolymers, polybutadiene, silicone rubber, neoprene, fluoroelastomers and ethylene-vinyl acetate copolymer.

27. A modified polymer having enhanced oxidative stability and having modified molecular weight and modified molecular weight distribution as a result of being treated in a process as defined in claim 1.

28. A modified polymer having enhanced oxidative stability, and having modified molecular weight and modified molecular weight distribution as a result of having been treated in a process as defined in claim 2.

29. A cross-linked olefin derived polymer having enhanced oxidative stability made by a process as defined in claim 1.

30. A cross-linked polymer as defined in claim 29 selected from the group consisting of chlorinated polyethylene, low density polyethylene, linear low density polyethylene, and high density polyethylene.

31. A cross-linked olefin derived polymer having enhanced oxidative stability made by a process as defined in claim 2.

32. A cross-linked polymer as defined in claim 31 selected from the group consisting of chlorinated polyethylene, low density polyethylene, linear low density polyethylene, and high density polyethylene.

* * * * *